US00PP13676P29

(12) United States Plant Patent
Coiner

(10) Patent No.: US PP13,676 P2
(45) Date of Patent: Mar. 25, 2003

(54) SHRUB ROSE PLANT NAMED 'COISTOR'

(75) Inventor: James Coiner, La Verne, CA (US)

(73) Assignee: Coiner Nursery, LaVerne, CA (US)

( * ) Notice: Subject to any disclaimer, the term of this patent is extended or adjusted under 35 U.S.C. 154(b) by 0 days.

(21) Appl. No.: 09/483,453

(22) Filed: Jan. 12, 2000

(51) Int. Cl.[7] ..... A01H 5/00

(52) U.S. Cl. ..... Plt./102

(58) Field of Search ..... Plt./102, 101, 103, Plt./104, 106, 107

*Primary Examiner*—Bruce R. Campell
*Assistant Examiner*—June Hwu
(74) *Attorney, Agent, or Firm*—Christie, Parker & Hale, LLP

(57) ABSTRACT

A shrub rose plant variety producing red/pink tinged white flowers.

1 Drawing Sheet

BACKGROUND OF THE INVENTION

The present invention relates to a new and distinct shrub rose variety of the species *Rosaceae Rosa,* which was originated by my crossing as seed and pollen parents two unnamed, undistributed, unpatented seedlings. The varietal denomination of this new rose is 'COISTOR'.

SUMMARY OF THE INVENTION

Among the novel characteristics possessed by the new variety which distinguish it from its parents and all other varieties of which I am aware are its attractive white flowers tinged with red/pink.

Asexual reproduction by budding of the new variety as performed in Watsonville, Calif., shows that the foregoing and other distinguishing characteristics come true to form and are established and transmitted through succeeding propagations. Other known forms of asexual reproduction may be also used.

COMPARISON WITH PARENT

The new variety distinguishes from its parent in flower size and color.

BRIEF DESCRIPTION OF ILLUSTRATION

The accompanying illustration shows typical two-year old specimens of the vegetative growth and flowers of the new variety in different stages of development and depicted in color as nearly true as it is reasonably possible to make the same in a color illustration of this character.

DESCRIPTION OF THE NEW VARIETY

The following is a detailed description of the new variety, from specimens grown outdoors in Kern County, Calif., in the month of November. The color terminology used is in accordance with *The Royal Horticultural Society Colour Chart* (R.H.S.C.C.), and refers to plate numbers in the aforementioned color chart. Phenotypic expression may vary depending on light, environmental and cultural conditions.

Flower:

*Habit.*—Blooms continuously.

*Bud.*—Surface texture of upper and lower surfaces is smooth, color is near 158C on top surface and near 147C on bottom surface, without anthocyanin intonations. Size: 1½ inches long by about 1¼ inches wide. Form: Globular. Color: When sepals first divide near 68A.

*Sepals.*—About 1 inch in length; about ¾ length of bud.

*Peduncle.*—Length: About ¾ inches. Strength: Erect, sturdy. Color: Some anthocyanin and intonation, color near 179B.

Bloom:

*Size.*—About 2¾ inch diameter.

*Borne.*—Singly.

*Form.*—Flat, round.

*Petalage.*—About 21.

*Color (⅓ to ½ open).*—Outer petals: Top surface near 69D; under surface near 62B. Inner Petals: Top surface near 62A; under surface near 62A. Base of petals: Near 75C on top and bottom surfaces. General tonality from a distance: Pink to white.

*Color change.*—Fades to white upon aging. Petals: Top and bottom surface near white; general tonality from a distance is white, outer petals becoming near 27D in color; inner petals near 27A.

Petals: Length about 1½ inches, width about ¾ inch, rounded.

*Texture.*—Average.

*Appearance.*—Velvety.

*Form.*—Rounded.

*Arrangement.*—Imbricated, shingle-like.

*Petaloids in center.*—None.

*Persistence.*—Petals drop off cleanly.

*Fragrance.*—Slight.

*Lasting quality.*—Up to 4 days.

Reproductive organs:

*Stamens, filaments and anthers.*—About 43 stamens and about 17 pistils.

*Arrangement.*—Interferingly arranged.

*Color.*—Stamens: Near 11C, about 1/16 inch. Anthers: Near 21A, about 1/16 inch.

*Pollen.*—Color: Near 21B.

*Styles.*—Uneven, about ⅛ inch to 1/16 inch in length, color near 47C.

*Stigmas.*—Color: Near 20C.

*Hips.*—Does not set hips.

Plant:

*Form*.—Upright, compact, about 37 inches high, by about 21 inches wide.

*Growth*.—Uniform branching, about 26 inches high first season.

*Foliage*.—Compound 3 or 5 leaflets about 1¼ inches long by about 9/16 inch wide, smooth, pointed. Size: About 2½ inches long by about 1 9/16 inches wide. Quantity: Average. Color New foliage: Upper side near 59C; underside near 62D. Old foliage: Upper side near 138A; underside near 138D. Shape: Rounded. Texture: Upper side smooth. Edge: Serrated. Serration: Serrate. Disease Resistance: Very resistant to mildew, blackspot and rust.

*Anthocyanin coloration*.—No anthocyanin coloration was observed.

*Wood*.—New shoots: Near 145B, smooth. Old wood: Near 147A, smooth.

*Thorns*.—Quantity: Average. Form: Straight. Length: Short. Color when young: Near 178D. Position: About ¼ inch long, color near 165B, pointed.

*Prickles*.—None.

*Flower stems*.—Usually about 10 inches.

*Stipules*.—Short, pointed, color near 142C.

Winter hardiness: Completely winter hardy in Kern County, Calif.

I claim:

1. A new and distinct shrub rose plant of the variety substantially as shown and described.

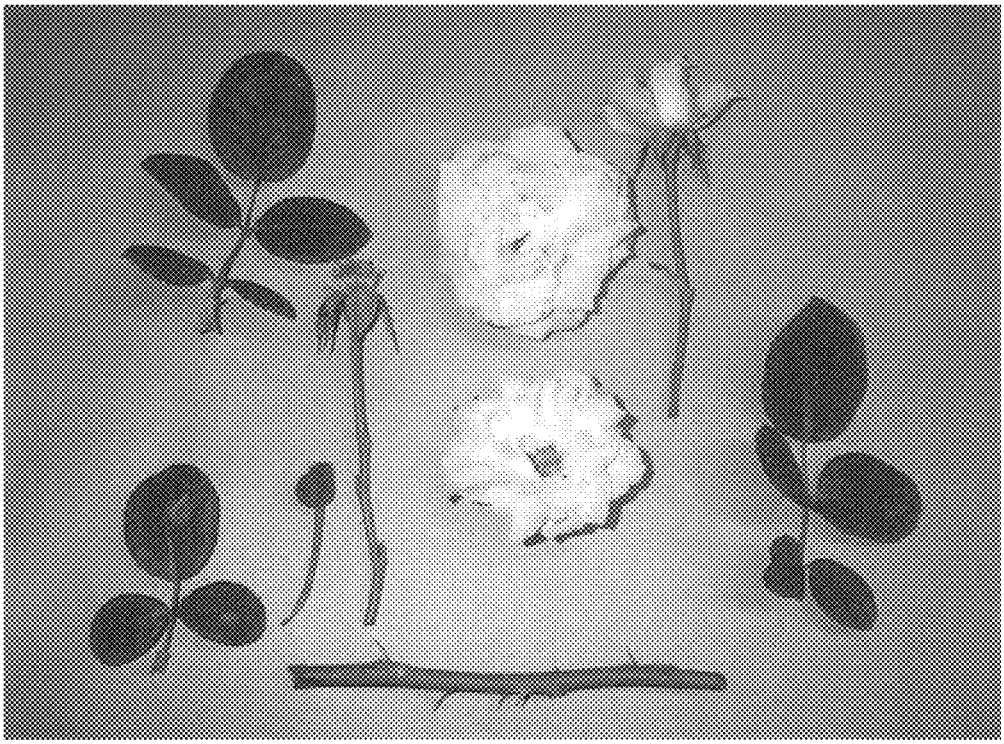

* * * * *